(12) United States Patent
Wigand et al.

(10) Patent No.: US 9,291,690 B2
(45) Date of Patent: Mar. 22, 2016

(54) SYSTEM AND METHOD FOR DETERMINING MOLECULAR STRUCTURES IN GEOLOGICAL FORMATIONS

(75) Inventors: Marcus Oliver Wigand, Missouri City, TX (US); Boqin Sun, Concord, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 928 days.

(21) Appl. No.: 13/530,766

(22) Filed: Jun. 22, 2012

(65) Prior Publication Data

US 2013/0342201 A1 Dec. 26, 2013

(51) Int. Cl.
*G01N 24/08* (2006.01)
*G01R 33/46* (2006.01)
*A47J 47/14* (2006.01)
*A45C 11/20* (2006.01)

(52) U.S. Cl.
CPC ............ *G01R 33/4633* (2013.01); *A45C 11/20* (2013.01); *A47J 47/14* (2013.01); *G01N 24/081* (2013.01)

(58) Field of Classification Search
CPC .. G01N 24/081; G01R 33/4633; A45C 11/20; A47J 47/14
USPC ...................... 436/29, 31, 173; 702/11, 27, 32
See application file for complete search history.

(56) References Cited

U.S. PATENT DOCUMENTS

2003/0214287 A1 11/2003 Sun et al.

OTHER PUBLICATIONS

Pugmire, R. J. et al, in"Chemistry and Characterization of Coal Macerals" Chapter 6, ACS Symposium Series Winans, R. et al, editors, American Chemical Society, Washington, DC, 1984, 79-97.*
Soderquist, A. et al, Energy & Fuels 1987, 1, 50-55.*
Franco, D. V. et al, Energy & Fuels 1991, 5, 527-533.*
Nomura, M.. et al, Energy & Fuels 1998, 12, 512-523.*
Pekerar, S. et al, Energy & Fuels 1999, 13, 305-308.*
Lupulescu, A. et al, Journal of the American Chemical Society 2003, 125, 3376-3383.*
Mao, J. et al, Organic Geochemistry 2011, 42, 891-902.*
Boqin Sun, Bob Carlson, Marcus O. Wigand, Using Laplace Inversion to Derive Kerogen Structural Parameters from Solid-state NMR Spectra, Chevron Tech Report.
Solum, M.S., Pugmire, R.J., (1989). 13C Solid-State NMR of Argone Premium Coals. Energy & Fuels 3, 187-193.
Hu, Jian Zhi, et al.; "Structural Determination in Carbonaceous Solids Using Advanced Solid State NMR Techniques"; XP002713083, Energy & Fuels, 2001, vol. 15, pp. 14-22.
Sullivan, Mark J., et al.; "Spin Dynamics in the Carbon-13 Nuclear Magnetic Resonance Spectrometric Analysis of Coal by Cross Polarization and Magic-Angle Spinning"; Analytical Chemistry, Aug. 1982, vol. 54, pp. 1615-1623.

(Continued)

*Primary Examiner* — Arlen Soderquist
(74) *Attorney, Agent, or Firm* — Ben Esplin; Marie L. Clapp

(57) ABSTRACT

Molecular structures of organic molecules in a geological formation are determined. The organic molecules may include kerogen, coal, and/or other organic molecules. In particular, the technique implemented may operate to convert nuclear magnetic resonance data into a multi-dimensional space that permits identification of molecular structures through comparisons of intensity information across the multi-dimensional space with a cutoff map of the space. This may not only simplify the identification of molecular structures of the organic molecules, but also use exact mathematical model for mixture samples to derive both structural and dynamic parameters plus their variation.

6 Claims, 9 Drawing Sheets

(56) References Cited

OTHER PUBLICATIONS

Zujovic, Zoran, et al.; "Structural Analysis of Aleksinac Oil Shale Kerogen by High-Resolution Solid-State $^{13}$C n.m.r. Spectroscopy"; XP002713082, Fuel, 1995, vol. 74, No. 12, pp. 1903-1909.

International Search Report, issued on Oct. 2, 2013 during the prosecution of International Application No. PCT/US2013/045924.
Written Opinion of the International Searching Authority, issued on Oct. 2, 2013 during the prosecution of International Application No. PCT/US2013/045924.

* cited by examiner

SYSTEM AND METHOD FOR DETERMINING MOLECULAR STRUCTURES IN GEOLOGICAL FORMATIONS

FIELD

The disclosure relates to the determination of molecular structures of organic molecules in a geological formation through analysis of nuclear magnetic resonance measurements.

BACKGROUND

The determination of molecular structures of organic molecules in a geological formation, such as kerogen or coal, is known. Some of these conventional determinations are based on nuclear magnetic resonance measurements taken at the geological formation.

A first step in a convention technique a high-resolution $^{13}C$ CP/MAS spectrum of a given sample is obtained, and then a plurality of different cutoffs are applied to the spectrum in discrete processes in order to determine the mole fraction of different sets of molecular structures and dynamics (e.g., aromatic and aliphatic carbons; methyl group, ethylene/methine group, and methoxy group in aliphatic regime; carbonyl carbons and aromatic carbons; aldehyde/ketone and acid/ester amide groups; protonated and non-protonated aromatic rings; and bridge heads, alkyl-attached aromatic rings, and phenols/phenolic esters; and/or other structures). These discrete processes can time-consuming and costly with respect to computing and/or human resources. Conventional techniques may assume NMR spectra comes from a pure sample that all molecules have same structure. Conventional techniques typically do not measure and/or use the shapes of static and dynamic parameter distributions, which characterize the heterogeneity of molecular structures and variation of molecular mobility.

One aspect of the disclosure relates to a computer-implemented method of determining molecular structures of organic molecules in a geological formation. The method is implemented in a computer system comprising one or more physical processors configured to execute computer program modules. The method comprises obtaining a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum; applying a transformation to the plurality of chemical shift spectra that yields a multi-dimensional distribution of intensity as a function of chemical shift and one or more dynamic parameters of the nuclear magnetic resonance measurements, wherein the transformation is applied individually to separate sets of chemical shift measurements having common chemical shift values such that the transformation comprises for a given chemical shift value: obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform; and determining molecular structures of the organic molecules in the geological formation based on an analysis of the multi-dimensional distribution of intensity and its shape.

A system configured to determine molecular structures of organic molecules in a geological formation. The system comprising one or more processors configured to execute computer program modules. The computer program modules comprising a spectrum module, a transformation module, and an analysis module. The spectrum module is configured to obtain a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum. The transformation module is configured to apply a transformation to the plurality of chemical shift spectra that yields a multi-dimensional distribution of intensity as a function of chemical shift and one or more dynamic parameters of the nuclear magnetic resonance measurements. The transformation module is configured such that the transformation is applied individually to separate sets of chemical shift measurements having common chemical shift values such that the transformation comprises for a given chemical shift value: obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform. The analysis module is configured to determine molecular structures of the organic molecules in the geological formation based on an analysis of the multi-dimensional distribution of intensity.

Non-transitory electronic storage media storing processor executable instructions configured to cause one or more processors to execute a method of determining molecular structures of organic molecules in a geological formation. The method comprising obtaining a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum; applying a transformation to the plurality of chemical shift spectra that yields a multi-dimensional distribution of intensity as a function of chemical shift and one or more dynamic parameters of the nuclear magnetic resonance measurements, wherein the transformation is applied individually to separate sets of chemical shift measurements having common chemical shift values such that the transformation comprises for a given chemical shift value: obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform; and determining molecular structures of the organic molecules in the geological formation based on an analysis of the multi-dimensional distribution of intensity.

These and other objects, features, and characteristics of the system and/or method disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
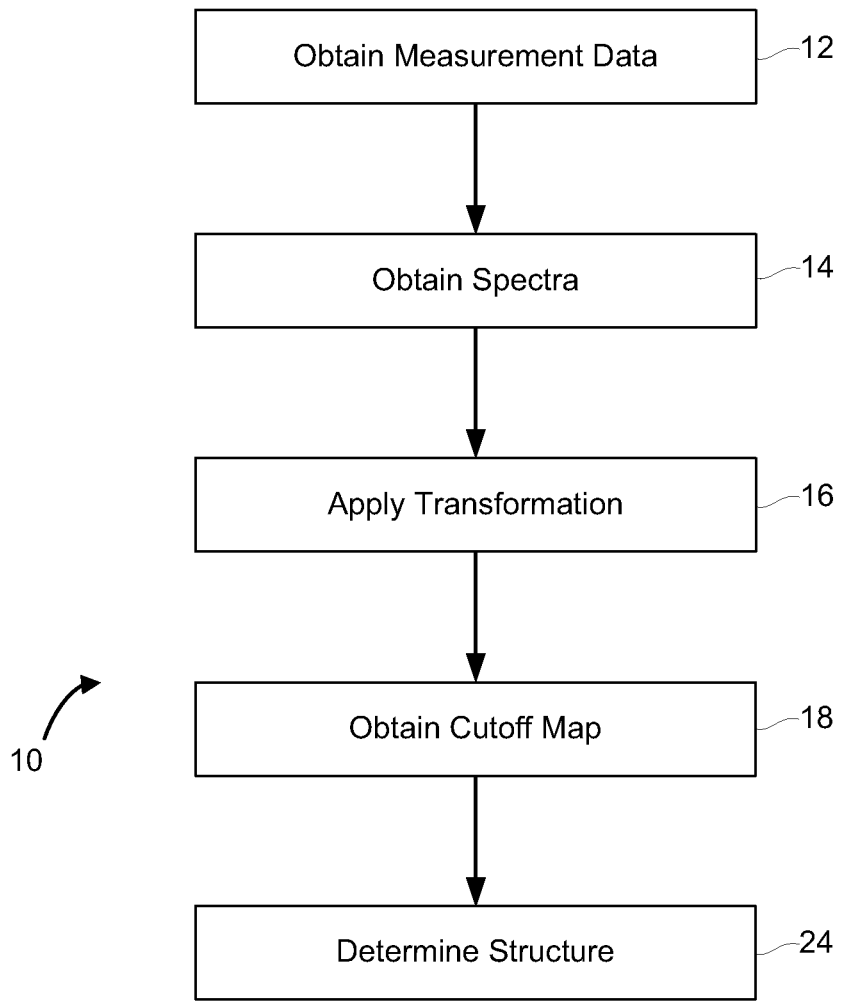
FIG. 1 illustrates a method of determining molecular structures of organic molecules in a geological formation.

The present technology may be described and implemented in the general context of a system and computer methods to be executed by a computer. Such computer-executable instructions may include programs, routines, objects, components, data structures, and computer software technologies that can be used to perform particular tasks and process abstract data types. Software implementations of the present technology may be coded in different languages for application in a variety of computing platforms and environments. It will be appreciated that the scope and underlying principles of the present technology are not limited to any particular computer software technology.

Moreover, those skilled in the art will appreciate that the present technology may be practiced using any one or combination of hardware and software configurations, including but not limited to a system having single and/or multi-processer computer processors system, hand-held devices, programmable consumer electronics, mini-computers, mainframe computers, and the like. The technology may also be practiced in distributed computing environments where tasks are performed by servers or other processing devices that are linked through one or more data communications networks. In a distributed computing environment, program modules may be located in both local and remote computer storage media including memory storage devices.

Also, an article of manufacture for use with a computer processor, such as a CD, pre-recorded disk or other equivalent devices, may include a computer program storage medium and program means recorded thereon for directing the computer processor to facilitate the implementation and practice of the present technology. Such devices and articles of manufacture also fall within the spirit and scope of the present technology.

Referring now to the drawings, embodiments of the present technology will be described. The technology can be implemented in numerous ways, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the present technology are discussed below. The appended drawings illustrate only typical embodiments of the present technology and therefore are not to be considered limiting of its scope and breadth.

FIG. 1 illustrates a method 10 of determining molecular structures of organic molecules in a geological formation. The organic molecules may include kerogen, coal, and/or other organic molecules. In particular, method 10 may operate to convert nuclear magnetic resonance data into a multi-dimensional space that permits identification of molecular structures through comparisons of intensity and shape information across the multi-dimensional space with a cutoff map of the space. This may not only simplify the identification of molecular structures of the organic molecules, but also use exact mathematical model for mixture samples to derive both structural and dynamic parameters plus their variation. Whereas prior art uses only mathematical equations for a pure sample and does not consider any variation.

At an operation 12, nuclear magnetic resonance data for the geological formation is obtained. Obtaining the nuclear magnetic resonance data may include performing a nuclear magnetic resonance measurement, deriving information from a nuclear magnetic resonance measurement, accessing previously stored nuclear magnetic resonance data, receiving user input of nuclear magnetic resonance data, and/or other techniques for obtaining nuclear magnetic resonance data.

Nuclear magnetic resonance data is generated by performing nuclear magnetic resonance measurement on a geological formation. Nuclear magnetic resonance measurement typically involves two phases, polarization and acquisition. During polarization, one or more magnetic fields are applied to the geological formation to orient the hydrogen atoms within the geological formation. This may include applying a static magnetic field to provide an initial orientation to the hydrogen atoms, followed by the application of one or more dynamic magnetic fields (e.g., an oscillating magnetic field). The dynamic magnetic field(s) cause the hydrogen atoms to precess, which produces a signal. The decay of this signal is what is measured by the nuclear magnetic resonance measurement. This measurement may include the determination of one or more dynamic parameters that characterize the connectivity and/or mobility of atoms or nuclei in a molecule. The dynamic parameters may include, for example, one or more of dipolar dephasing time constant, a rotating-frame longitudinal relaxation time, a cross polarization transfer time constant, and/or other dynamic parameters. Their values reflect the mobility of molecules and their shapes denote the variation of the mobility due to variation of molecular structures. The nuclear magnetic resonance data obtained at operation 12 may include measurements, and/or information derived therefrom, taken for a plurality of different lengths of mixing times. For example, measurements may be taken with different contacting times during the mixing period, different dipolar dephasing times during the mixing period, and/or other different mixing times. The nuclear magnetic resonance measurements may be taken in a dipolar dephasing experiment under magic angle spinning framework, in a regular cross polarization experiment under magic angle spinning framework, and/or in other nuclear magnetic resonance experiments and/or frameworks.

At an operation 14, a plurality of chemical shift spectra are obtained. Individual ones of the chemical shift spectra are derived from nuclear magnetic resonance measurements taken at the geological formation for a plurality of different mixing times. The chemical shift spectra indicates intensity as a function of chemical shift. The chemical shift corresponds to the resonant frequency of a nucleus relative to a standard, as indicated by the nuclear magnetic resonance data. Chemical shift values are used as a fingerprinting of a molecule in the structural determination due to its uniqueness. And its variation of single peak indicates the variation of similar molecular structures.

Figure 2:
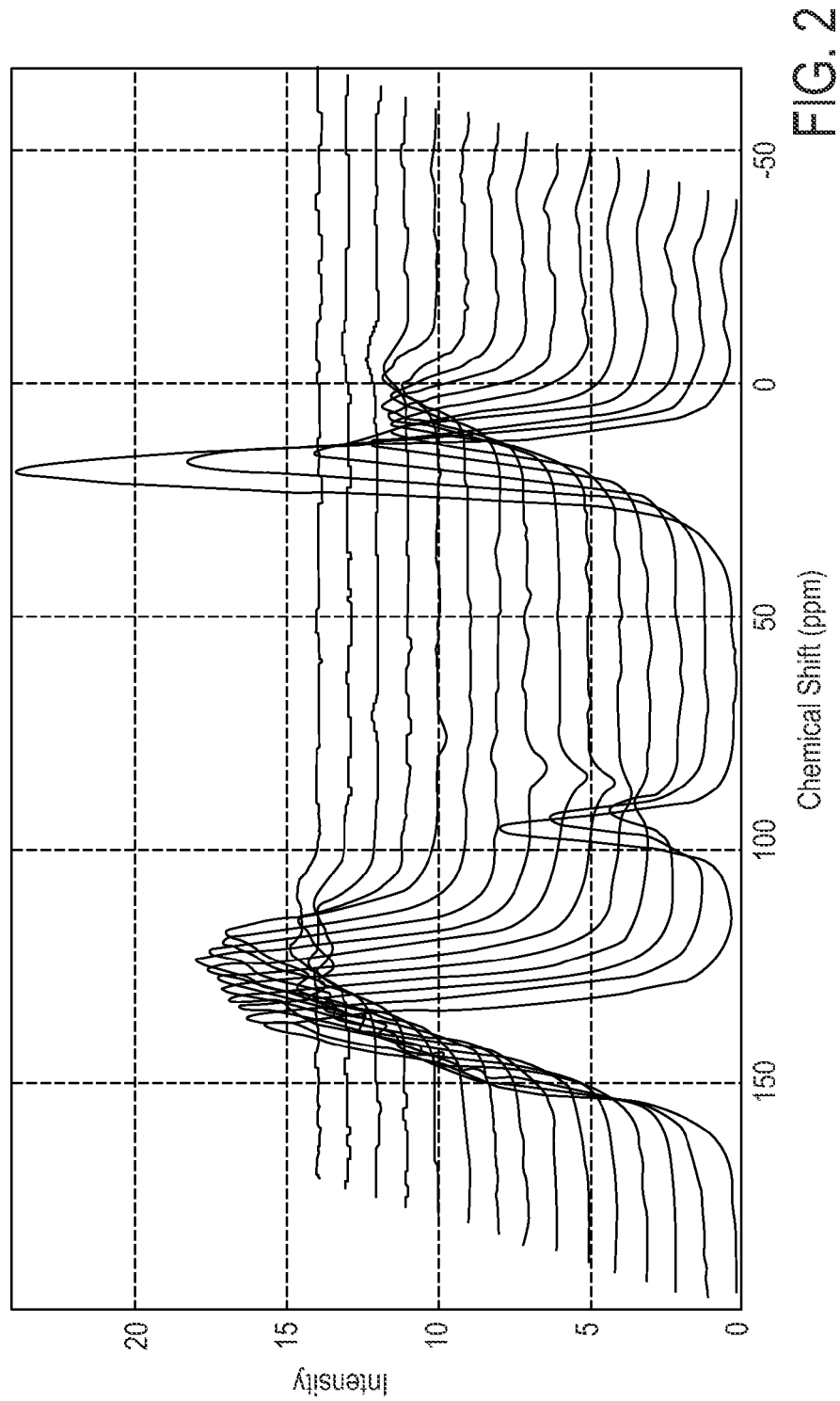
FIG. 2 illustrates a plurality of plots of chemical shift spectra, with each spectrum corresponding to a different length of a mixing time.

By way of illustration, FIG. 2 shows a plurality of plots of chemical shift spectra, with each spectrum corresponding to a different mixing time. In some implementations, the plots shown in FIG. 2 correspond to chemical shift spectra derived from nuclear magnetic resonance measurements taken in a dipolar dephasing experiment under magic angle spinning framework with different dipolar dephasing times. The individual spectra correspond to individual dipolar dephasing times.

Figure 3:
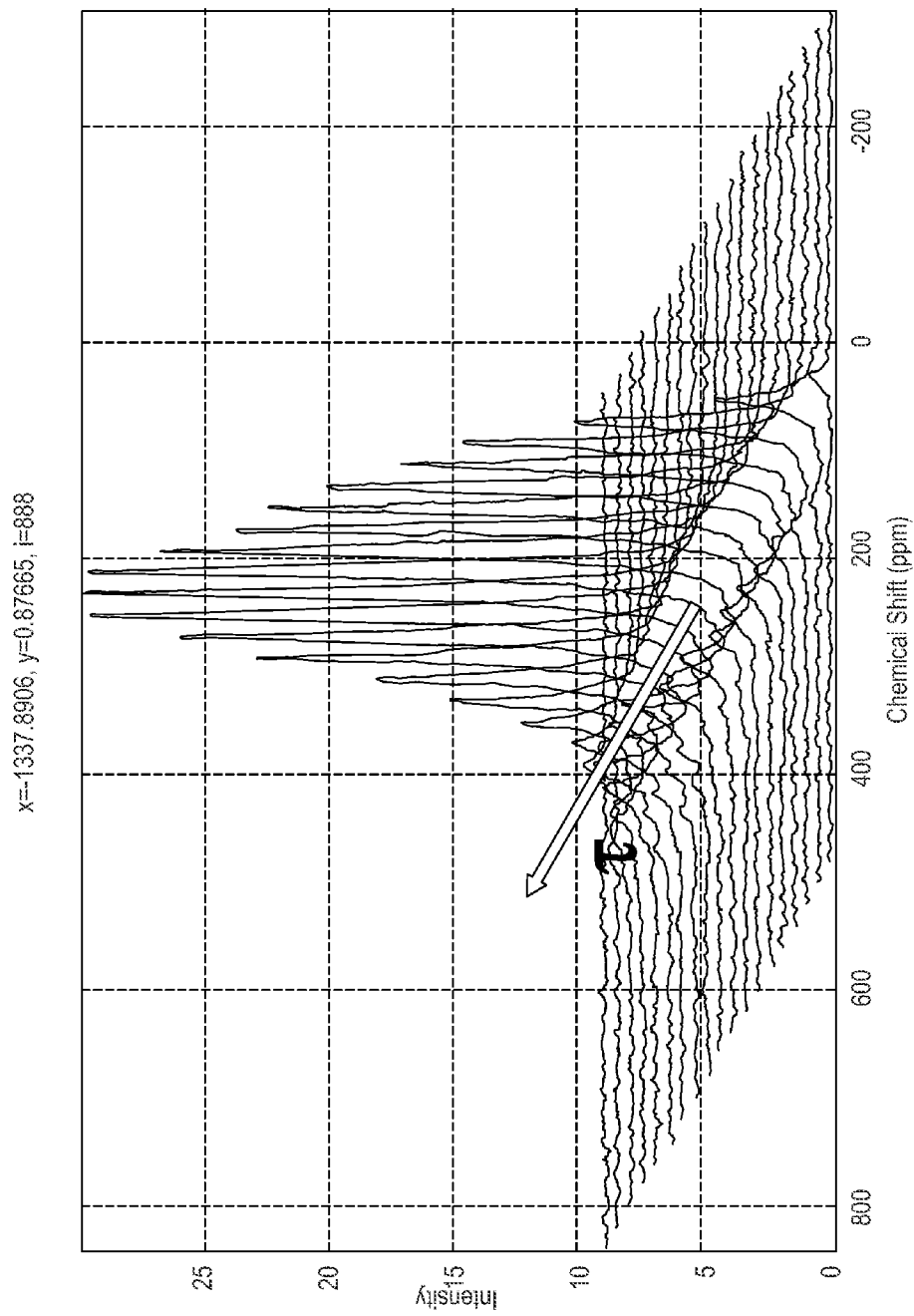
FIG. 3 illustrates a plurality of plots of chemical shift spectra, with each spectrum corresponding to a different length of a mixing time.

As another illustration, FIG. 3 shows a plurality of plots of chemical shift spectra from a different set of nuclear magnetic resonance data. The plots shown in FIG. 3 have been derived from nuclear magnetic resonance measurements taken in a regular cross polarization experiment under magic angle spinning framework with different contacting times. The individual spectra correspond to individual contacting times.

Returning to FIG. 1, at an operation 16, a transform is applied to the plurality of chemical shift spectra that yields a multi-dimensional distribution of intensity as a function of chemical shift and one or more dynamic parameters that characterize the connectivity and/or mobility of atoms or nuclei in a molecule. Some implementations of the transform are described herein with respect to FIG. 6.

Figure 4:
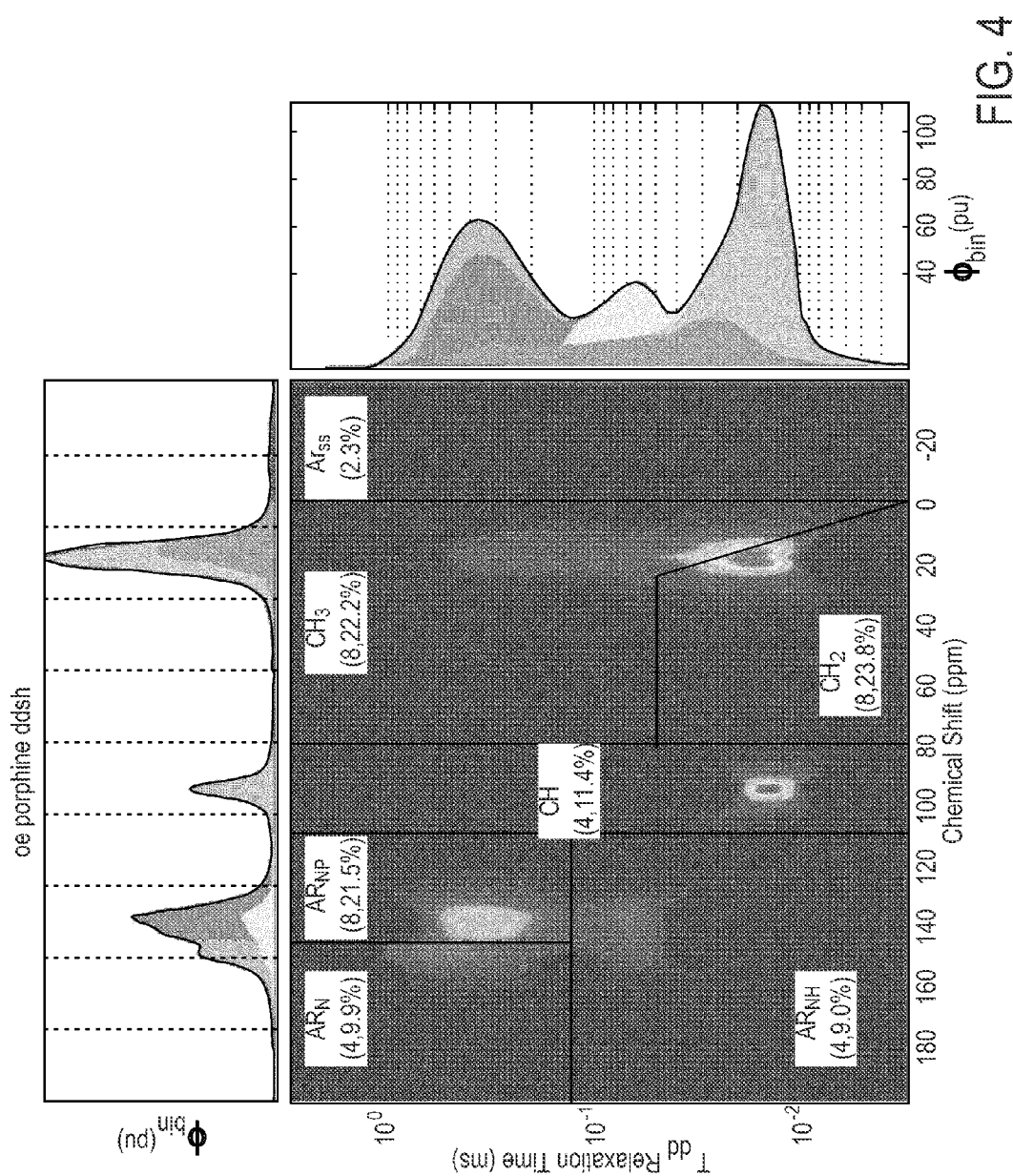
FIG. 4 illustrates a two-dimensional distribution of intensities.
Figure 5A:
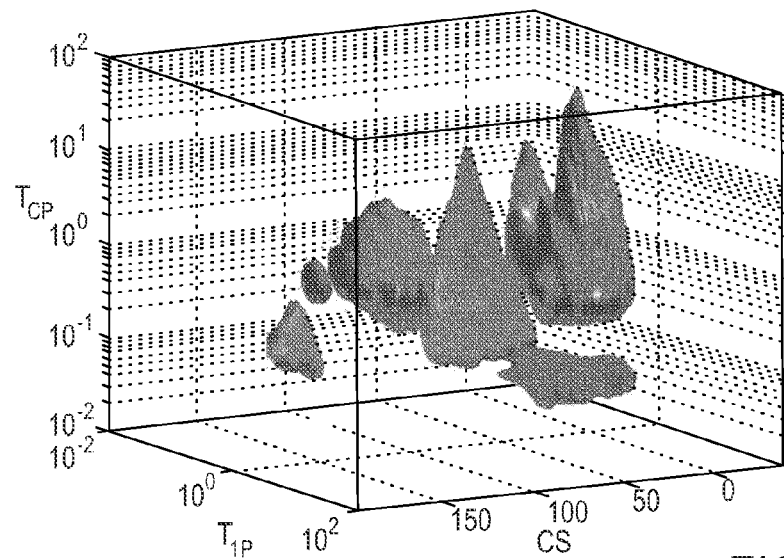
FIG. 5 illustrates a three-dimensional distribution of intensities.
Figure 5B:
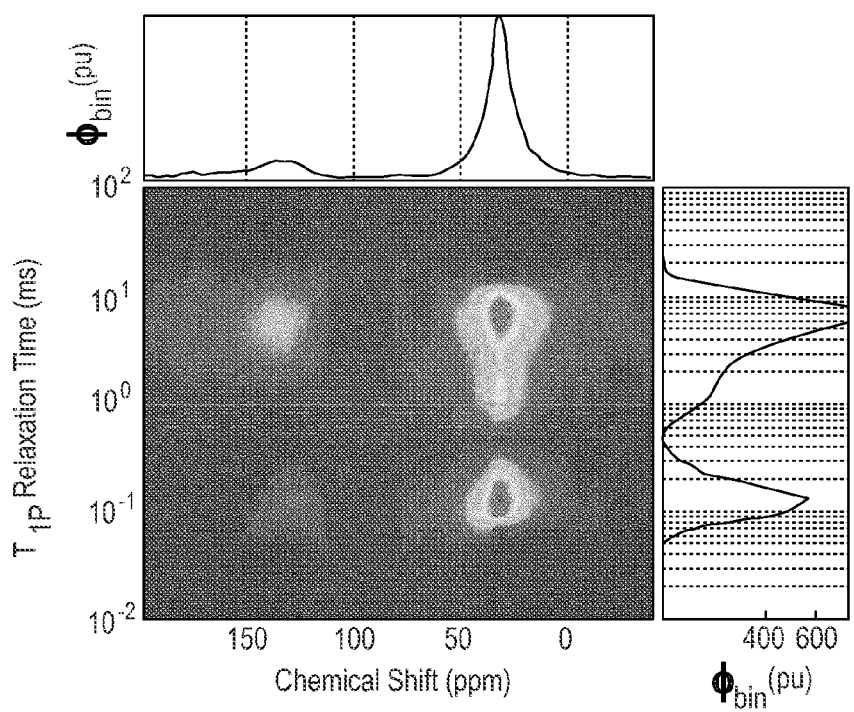
Figure 5C:
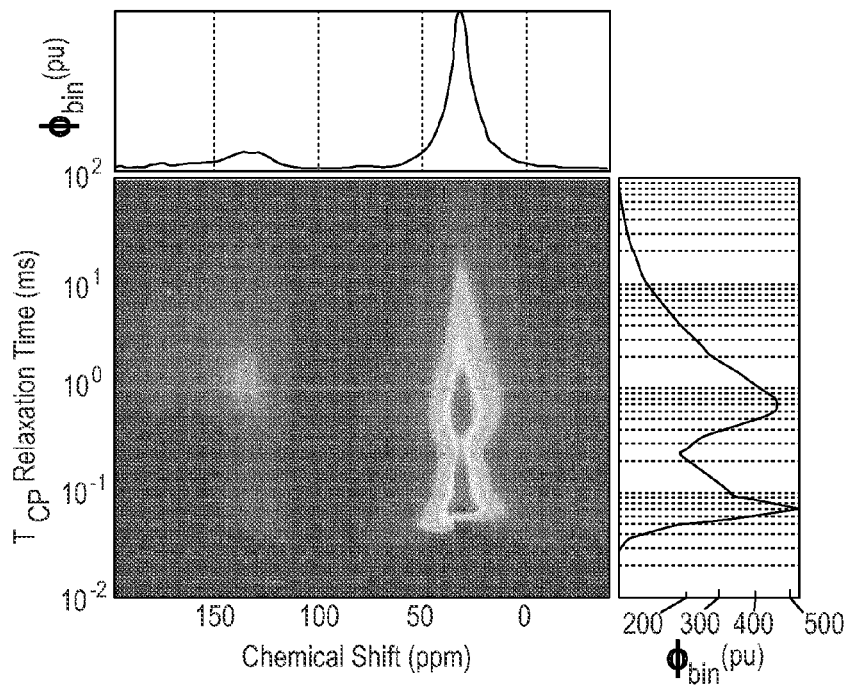
Figure 5D:
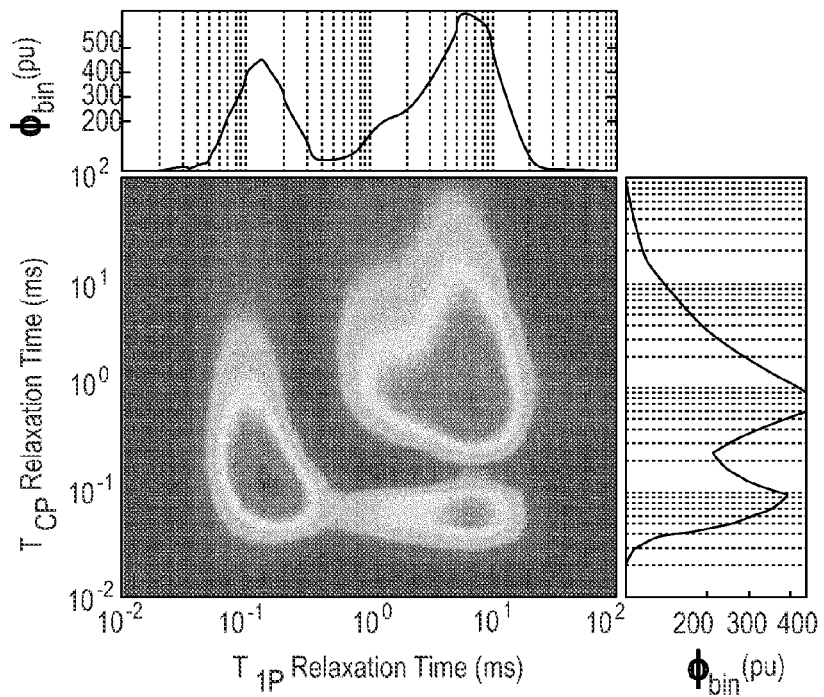

By way of illustration, FIG. 4 depicts a two-dimensional distribution of intensities (with intensity denoted by shade). The two-dimensional distribution is parameterized by chemical shift and a dynamic parameter. The dynamic parameter in the illustrated example is a dipolar dephasing time constant. The distribution of intensities shown in FIG. 4 may be the result of performing the transform on the chemical shift spectra depicted in FIG. 2.

As another illustration, FIG. 5 depicts a three-dimensional distribution of intensities (with intensity denoted by color). The three-dimensional distribution is parameterized by chemical shift and two dynamic parameters. The two dynamic parameters are rotating-frame longitudinal relaxation time and cross polarization transfer time constant. The distribution of intensities shown in FIG. 5 may be the result of performing the transform on the chemical shift spectra depicted in FIG. 3.

Returning to FIG. 1, at an operation 18, a cutoff map for the multi-dimensional distribution of intensities generated at operation 16 may be obtained. The cutoff map may associate specific regions within the multi-dimensional distribution with specific molecular structures. An elevated intensity within a given region indicates the presence of molecular structures associated with the given region in the organic molecules in the geological formation. Obtaining a cutoff map may include determining the cutoff map based on distribution information (e.g., past nuclear magnetic resonance measurements and/or corresponding analysis, a calibration, and/or based on other information), accessing a previously generated cutoff map (e.g., from electronic storage, over a network, and/or from other sources), and/or obtaining the cutoff map from other sources.

Figure 6:
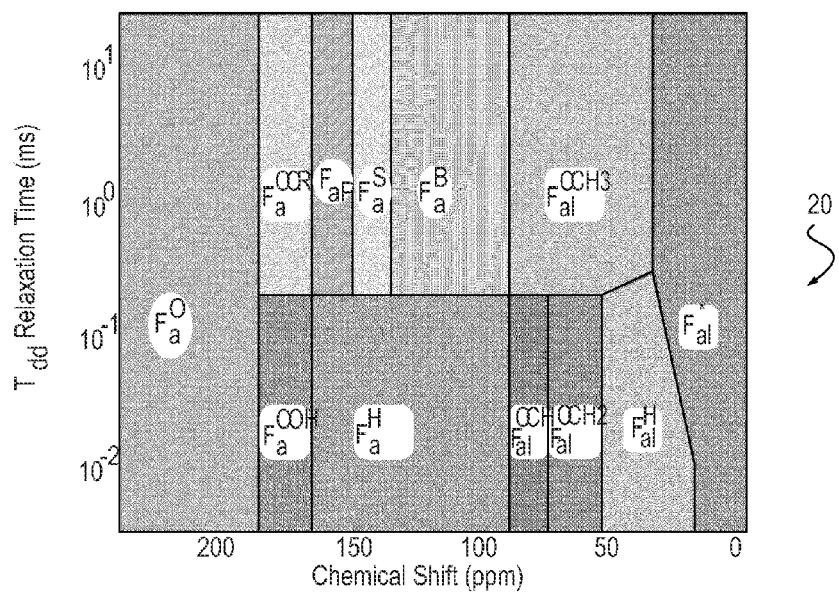
FIG. 6 illustrates a cutoff map for a two-dimensional distribution of intensities parameterized by chemical shift and a dipolar dephasing time constant.

By way of illustration, FIG. 6 shows a cutoff map 20 for a two-dimensional distribution of intensities parameterized by chemical shift and a dipolar dephasing time constant. Cutoff map 20 includes a plurality of regions 22, with the individual regions 22 corresponding to different molecular structures (e.g., as labeled in FIG. 6).

Figure 7:
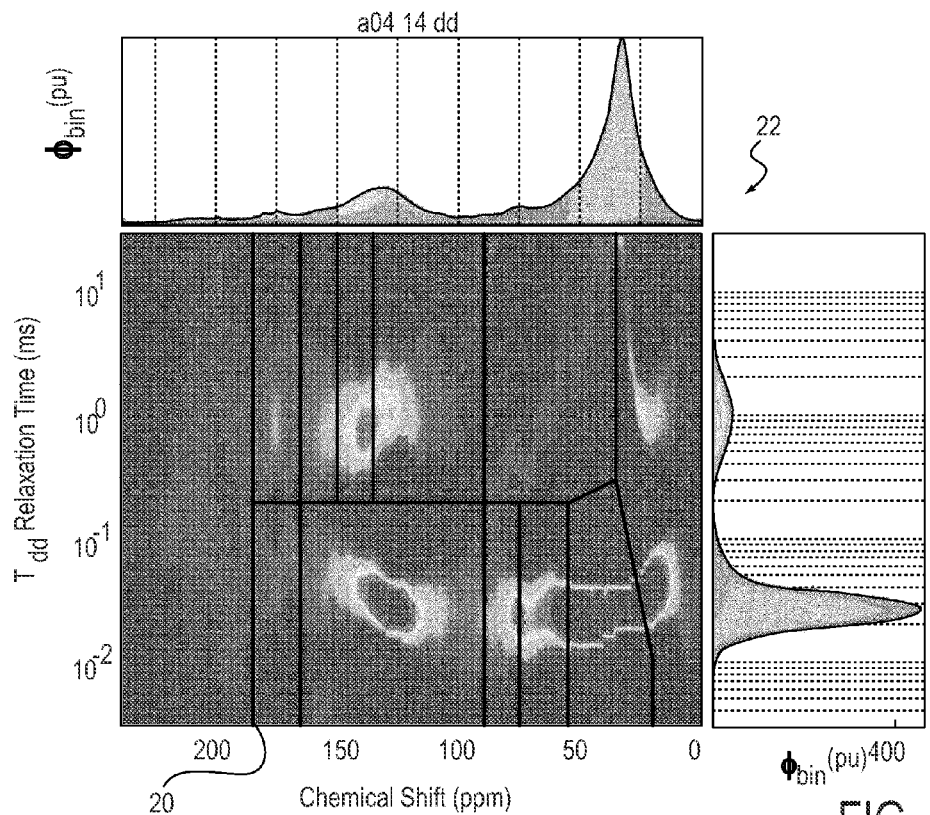
FIG. 7 illustrates a two-dimensional distribution of intensities.

FIG. 7 shows a two-dimensional distribution of intensities (e.g., generated by operation 16 shown in FIG. 1 and described herein) parameterized by chemical shift and a dipolar dephasing time constant, with intensity being denoted by shade. The plot is overlayed by cutoff map 20. Elevated intensities in individual ones of regions 22 of cutoff map 20 indicate the presence of the molecular structures in the geological formation corresponding to the regions 22 in which intensity is elevated.

Returning to FIG. 1, at an operation 24, the molecular structures present in the geological formation are identified based on the multi-dimensional distribution generated at operation 16 and the cutoff map obtained at operation 18. This identification is performed by determining for which regions in the cutoff map intensity is elevated. Detections of elevated intensity may be made automatically and/or manually through visual inspection. As a non-limiting example, an elevated intensity may be identified by an individual intensity reading above a threshold intensity, an aggregation of the intensities within the given region (e.g., an average, a weighted average, and/or other aggregations) that breach a threshold level, and/or other analytical tools for identifying an elevated intensity within the given region.

Figure 8:
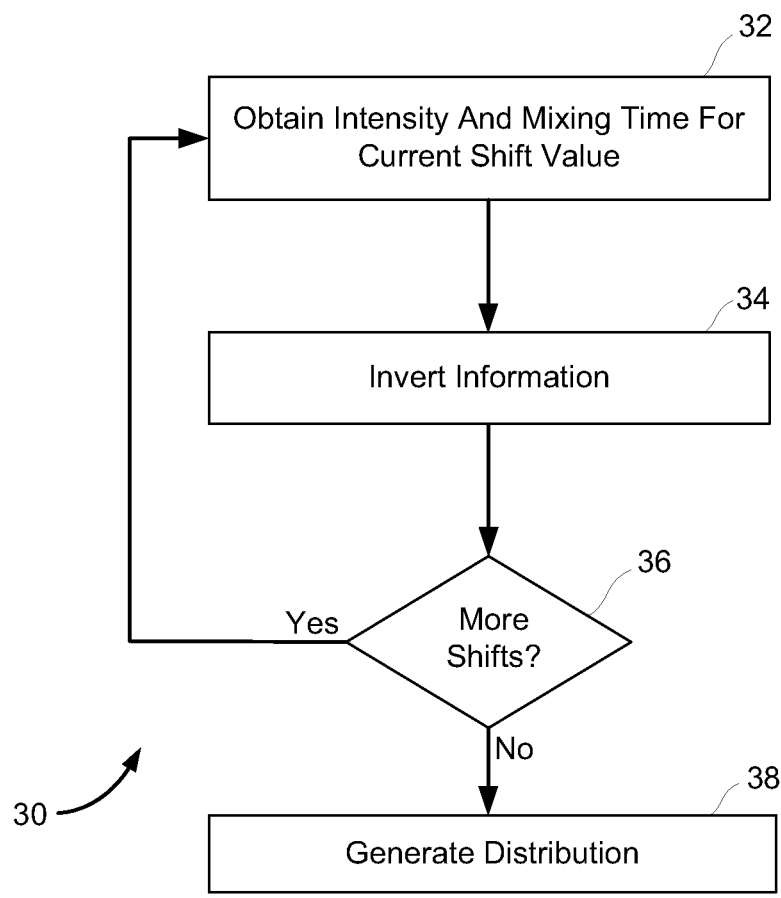
FIG. 8 illustrates a method of transforming chemical shift information into a multi-dimensional distribution of intensities parameterized by chemical shift and one or more dynamic parameters.

FIG. 8 illustrates a method 30 of transforming chemical shift information into a multi-dimensional distribution of intensities parameterized by chemical shift and one or more dynamic parameters. In some implementations, method 30 may be implemented as operation 16 of method 10 (shown in FIG. 1 and described herein). It will be appreciated that this is not intended to be limiting, as method 30 may be applied in a variety of other contexts. The input to method 30 includes a plurality of chemical shift spectra representing nuclear magnetic resonance measurements taken at different mixing times, such that individual ones of the spectra correspond to different mixing times. This may include, for example, a set of chemical shift spectra obtained at operation 14 of method 10 (shown in FIG. 1 and described herein).

At an operation 32, for a current chemical shift value, intensities and corresponding mixing times are obtained across the plurality of chemical shift spectra. This includes obtaining, for a given chemical shift spectrum, the intensity in the given chemical shift spectrum at the current chemical shift value and the length of the mixing time corresponding to the given chemical shift spectrum.

At an operation 34, the intensities and lengths of mixing time at the current chemical shift value are inverted to provide intensity as a function of one or more dynamic parameters that characterize the connectivity and mobility of atoms and/or nuclei in a molecule. The one or more dynamic parameters may characterize a specific type of nucleus in a molecule. The inversion may include performance of a Laplace transform on the intensities and lengths of mixing time. The dynamic parameters may include, for example, one or more of dipolar dephasing time constant, a rotating-frame longitudinal relaxation time, a cross polarization transfer time constant, and/or other dynamic parameters.

At an operation 36, a determination is made as to whether there are additional chemical shift values for which operations 32 and 34 have not been performed. Responsive to a determination that there are additional chemical shift values to be processed, method 30 returns to operation 32 for a next chemical shift value. Responsive to a determination that there are no additional chemical shift values to be processed, method 30 proceeds to an operation 38.

At operation 38, the intensities for the individual chemical shift values that are determined as a function of the one or more dynamic parameters are used to generate a multi-dimensional distribution of the intensities parameterized by chemical shift and the one or more dynamic parameters. As was discussed above, illustrative examples of such distributions are shown in FIGS. 4-6.

The operations of methods 10 and 30 presented herein are intended to be illustrative. In some embodiments, method 10 and/or 30 may be accomplished with one or more additional operations not described, and/or without one or more of the operations discussed. Additionally, the order in which the operations of method 10 and 30 are illustrated in FIGS. 1 and 8 and described herein is not intended to be limiting.

In some embodiments, method 10 and/or 30 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 10 and/or 30 in response to instructions stored electronically on an electronic storage medium. The one or more processing devices may include one or more devices configured through hardware, firmware, and/or software to be specifically designed for execution of one or more of the operations of method 10 and/or 30.

Figure 9:
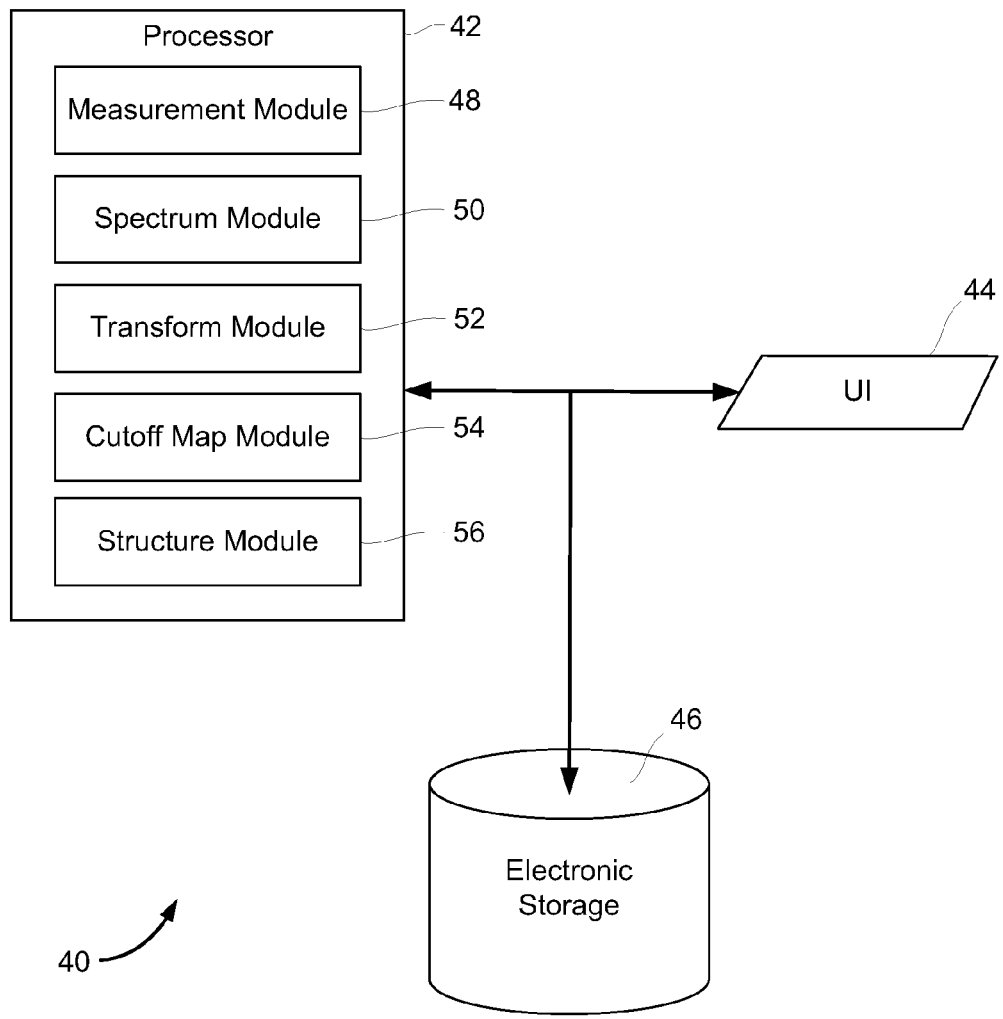
FIG. 9 illustrates a system configured to determine molecular structures of organic molecules in a geological formation.

FIG. 9 illustrates a system 40 configured to determine molecular structures of organic molecules in a geological formation. In some implementations, system 40 may include one or more of at least one processor 42, a user interface 44, electronic storage 46, and/or other components.

Processor 42 is configured to execute computer program modules. The computer program modules may include one or more of a measurement module 48, a spectrum module 50, a transform module 52, a cutoff map module 54, a structure module 56, and/or other modules.

Measurement module 48 is configured to obtain nuclear magnetic resonance data for the geological formation. In some implementations, measurement module 48 is configured to provide some or all of the functionality associated herein with operation 12 (shown in FIG. 1 and described herein).

Spectrum module 50 is configured to obtain a plurality of chemical shift spectra derived from nuclear magnetic resonance measurements. A set of chemical shift spectra are derived from nuclear magnetic resonance measurements taken at the geological formation for a plurality of different lengths of a mixing time. In some implementations, spectrum module 50 is configured to provide some or all of the functionality associated herein with operation 14 (shown in FIG. 1 and described herein).

Transform module 52 is configured to apply a transformation to the plurality of chemical shift spectra. The transformation yields a multi-dimensional distribution of intensities as a function of chemical shift and one or more dynamic parameters that characterize the connectivity and/or mobility of atoms or nuclei in a molecule. Transform module 52 is configured such that the transformation is applied individually to separate sets of chemical shift measurements having common chemical shift values. In some implementations, transform module 52 is configured to provide some or all of the functionality associated herein with operation 16 (shown in FIG. 1 and described herein) and/or method 30 (shown in FIG. 8 and described herein).

Cutoff map module 54 is configured to obtain a cutoff map for the multi-dimensional distribution of intensities generated by transform module 52. The cutoff map may associate specific regions within the multi-dimensional distribution with specific molecular structures. An elevated intensity and shape within a given region indicates the presence of molecular structures associated with the given region in the organic molecules in the geological formation. In some implementations, cutoff map module 54 is configured to provide some or all of the functionality associated with operation 18 (shown in FIG. 1 and described herein).

Structure module 56 is configured to determine molecular structures of the organic molecules in the geological formation based on an analysis of the multi-dimensional distribution of intensity and shape generated by transform module 52 and/or the cutoff map obtained by cutoff map module 54. In some implementations, structure module 56 is configured to provide some or all of the functionality associated with operation 24 (shown in FIG. 1 and described herein).

Processor 42 is configured to provide information processing capabilities in system 40. As such, processor 42 may include one or more of a digital processor, an analog processor, a digital circuit designed to process information, an analog circuit designed to process information, a state machine, and/or other mechanisms for electronically processing information. Although processor 42 is shown in FIG. 9 as a single entity, this is for illustrative purposes only. In some implementations, processor 42 may include a plurality of processing units. These processing units may be physically located within the same device, or processor 42 may represent processing functionality of a plurality of devices operating in coordination. Processor 42 may be configured to execute modules 48, 50, 52, 54, and/or 56 by software; hardware; firmware; some combination of software, hardware, and/or firmware; and/or other mechanisms for configuring processing capabilities on processor 42.

It should be appreciated that although modules 48, 50, 52, 54, and/or 56 are illustrated in FIG. 9 as being co-located within a single processing unit, in implementations in which processor 42 includes multiple processing units, one or more of modules 48, 50, 52, 54, and/or 56 may be located remotely from the other modules. The description of the functionality provided by the different modules 48, 50, 52, 54, and/or 56 described below is for illustrative purposes, and is not intended to be limiting, as any of modules 48, 50, 52, 54, and/or 56 may provide more or less functionality than is described. For example, one or more of modules 48, 50, 52, 54, and/or 56 may be eliminated, and some or all of its functionality may be provided by other ones of modules 48, 50, 52, 54, and/or 56. As another example, processor 42 may be configured to execute one or more additional modules that may perform some or all of the functionality attributed below to one of modules 48, 50, 52, 54, and/or 56.

Electronic storage 46 may comprise electronic storage media that electronically stores information. The electronic storage media of electronic storage 46 may include one or both of system storage that is provided integrally (i.e., substantially non-removable) with system 40 and/or removable storage that is removably connectable to system 40 via, for example, a port (e.g., a USB port, a firewire port, etc.) or a drive (e.g., a disk drive, etc.). Electronic storage 46 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 46 may include one or more virtual storage resources (e.g., cloud storage, a virtual private network, and/or other virtual storage resources). Electronic storage 46 may store software algorithms, information determined by processor 42, information received through user interface 44, and/or other information that enables system 40 to function as described herein.

Although the system(s) and/or method(s) of this disclosure have been described in detail for the purpose of illustration based on what is currently considered to be the most practical and preferred implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A computer-implemented method of determining molecular structures of organic molecules in a geological formation, the method being implemented in a computer system comprising one or more physical processors configured to execute computer program modules, the method comprising:

obtaining a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum and wherein the nuclear magnetic resonance measurements are obtained in a regular cross polarization experiment under magic angle spinning with a plurality of different contacting times during a mixing period;

applying a transformation to the plurality of chemical shift spectra that yields a multi-dimensional distribution of intensity as a function of chemical shift and one or more dynamic parameters of the nuclear magnetic resonance measurements, wherein the transformation is applied individually to separate sets of chemical shift measurements having common chemical shift values such that the transformation comprises for a given chemical shift value and wherein the multi-dimensional distribution is three-dimensional, and wherein the one or more dynamic parameters comprise a rotating frame longitudinal relaxation time and a cross polarization transfer time constant;

obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform; and determining molecular structures of the organic molecules in the geological formation based on an analysis of the multi-dimensional distribution of intensity and its shape.

2. The method of claim 1, wherein the one or more dynamic parameters include a dipolar dephasing time constant.

3. A system configured to determine molecular structures of organic molecules in a geological formation, the system comprising:

one or more processors configured to execute computer program modules, the computer program modules comprising:

a spectrum module configured to obtain a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum and wherein the nuclear magnetic resonance measurements are obtained in a regular cross polarization experiment under magic angle spinning with a plurality of different contacting times during a mixing period;

a transformation module configured to apply a transformation to the plurality of chemical shift spectra that yields a multi-dimensional distribution of intensity as a function of chemical shift and one or more dynamic parameters of the nuclear magnetic resonance measurements, wherein the transformation module is configured such that the transformation is applied individually to separate sets of chemical shift measurements having common chemical shift values such that the transformation comprises for a given chemical shift value and wherein the multi-dimensional distribution is three-dimensional, and wherein the one or more dynamic parameters comprise a rotating frame longitudinal relaxation time and a cross polarization transfer time constant;

obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform; and an analysis module configured to determine molecular structures of the organic molecules in the geological formation based on an analysis of the multi-dimensional distribution of intensity.

4. The system of claim 3, wherein the transformation module is configured such that the one or more dynamic parameters include a dipolar dephasing time constant.

5. Non-transitory electronic storage media storing processor executable instructions configured to cause one or more processors to execute a method of determining molecular structures of organic molecules in a geological formation, the method comprising:

obtaining a plurality of chemical shift spectra derived from nuclear magnetic resonance measurements taken at the geological volume of interest for a plurality of different lengths of a mixing time, wherein a given chemical shift spectrum has been derived from nuclear magnetic resonance measurements for a mixing time that corresponds to the given chemical shift spectrum and wherein the nuclear magnetic resonance measurements are obtained in a regular cross polarization experiment under magic angle spinning with a plurality of different contacting times during a mixing period;

applying a transformation to the plurality of chemical shift spectra that yields a multi-dimensional distribution of intensity as a function of chemical shift and one or more dynamic parameters of the nuclear magnetic resonance measurements, wherein the transformation is applied individually to separate sets of chemical shift measurements having common chemical shift values such that the transformation comprises for a given chemical shift value and wherein the multi-dimensional distribution is three-dimensional, and wherein the one or more dynamic parameters comprise a rotating frame longitudinal relaxation time and a cross polarization transfer time constant;

obtaining, from across the plurality of chemical shift spectra, the measurements of intensity at the given chemical shift value and the values of the mixing time at which the measurements were obtained; and inverting the measurements of intensity at the given chemical shift to provide intensity as a function of the one or more dynamic parameters for the given chemical shift, wherein such inversion comprises performance of a Laplace transform; and determining molecular structures of the organic molecules in the geological formation based on an analysis of the multi-dimensional distribution of intensity.

6. The storage media of claim 5, wherein the one or more dynamic parameters include a dipolar dephasing time constant.

* * * * *